United States Patent [19]

Satomura et al.

[11] Patent Number: 4,701,565

[45] Date of Patent: Oct. 20, 1987

[54] PROCESS FOR PREPARATION OF ETHERS

[75] Inventors: Masato Satomura; Ken Iwakura, both of Kanagawa; Hiroshi Kawakami, Shizuoka, all of Japan

[73] Assignee: Fuji Photo Film Co., Ltd., Kanagawa, Japan

[21] Appl. No.: 838,861

[22] Filed: Mar. 12, 1986

[30] Foreign Application Priority Data

Mar. 13, 1985 [JP] Japan .................................. 60-50138
Apr. 30, 1985 [JP] Japan .................................. 60-93329
May 14, 1985 [JP] Japan .................................. 60-102200

[51] Int. Cl.$^4$ ............................................. C07C 41/16
[52] U.S. Cl. ....................................... 568/644; 558/44
[58] Field of Search ........................... 568/644; 558/44

[56] References Cited

U.S. PATENT DOCUMENTS 4,553,018 6/1984 Nelson ................................. 568/630

OTHER PUBLICATIONS

Voss et al, Chem. Abst., vol. 25, #1797-8, (1931).
Karrer, Organic Chemistry, (1950), 430-431.
Wagner et al, Synthetic Organic Chemistry, (1953), 229, 250, 823, 826.

Primary Examiner—James H. Reamer
Attorney, Agent, or Firm—Sughrue, Mion, Zinn, Macpeak & Seas

[57] ABSTRACT

A process for the preparation of ethers is described, comprising reacting an alcohol with an organic sulfonyl halide in a solvent in the presence of an alkali to form a sulfonate, and then reacting the sulfonate with a phenol, wherein the alkali is an inorganic base selected from hydroxides and carbonates of sodium and potassium, and the solvent is a polar solvent. These ethers are useful as additives for use in recording materials, particularly heat-sensitive recording materials.

24 Claims, No Drawings

PROCESS FOR PREPARATION OF ETHERS

FIELD OF THE INVENTION

The present invention relates to a process for the preparation of ethers, and more particularly to a process for preparing ethers which are useful as additives for use in recording materials, especially heat-sensitive recording materials.

BACKGROUND OF THE INVENTION

As a process for the preparation of ethers using phenol derivatives as starting materials, the Williamson synthesis is known in which halides are reacted in the presence of an alkali. The synthesis is described in *Organic Synthesis*, Vol. I, p. 435 (1941). In general, however, these halides are commercially available only with difficulty; in particular, halides containing an ether bond in the molecule thereof are impossible to use as industrial starting materials. Diphenoxyalkanes, which are more simple compounds, have been prepared by reacting alkyl dihalide with phenols. However, aromatic ethers having two or more —O— linkages, such as diaryloxy alkane, have not been synthesized under mild reaction conditions in high yield.

SUMMARY OF THE INVENTION

As a result of extensive investigations, it has been found that when specified combinations of alkali and solvent are employed, and further when preferred reaction temperatures are employed, ethers can be prepared without isolation of sulfonates, using as starting materials alcohols which are easily commercially available.

An object of the present invention is to provide a process whereby ethers can be prepared in a simplified manner using alcohols as starting materials.

Thus, the present invention is directed to a process for preparing an ether which comprises reacting an alcohol with an organic sulfonyl halide in a solvent in the presence of an alkali to form a sulfonate, and then reacting the sulfonate with a phenol, wherein the alkali is an inorganic base selected from hydroxides and carbonates of sodium and potassium, and the solvent is a polar solvent.

DETAILED DESCRIPTION OF THE INVENTION

The reaction of the present invention proceeds according to the following Scheme (I) or Scheme (II).

Scheme (I)

$R_1OH \xrightarrow{(1) R_2SO_2X} [R_1OSO_2R_2] \xrightarrow{(2) Ar_1OH} R_1OAr_1$ Scheme (II)

$HO-R_4OH \xrightarrow{(1) R_2SO_2X}$

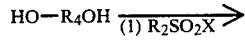

$[R_2SO_2O-R_4-OSO_2-R_2] \xrightarrow{(2) Ar_1OH}$ 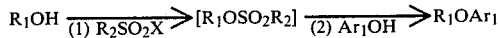 $Ar_1-O-R_4-O-Ar_1$ An alcohol used in the present invention includes $R_1OH$, or $HO-R_4-OH$.

$R_1OH$ preferably represents $Ar_2OR_3OH$. $R_2SO_2X$ (organic sulfonyl halide) represents an aliphatic or aromatic sulfonyl chloride. $Ar_1$ and $Ar_2$ each represents an aromatic ring which may be substituted with groups such as alkoxy, alkylthio, alkyl, alkenyl, acyl, cyano, hydroxy, halogen, aryl, aralkyl, and substituted amino. Most preferably $Ar_1$ and $Ar_2$ each represents a benzene ring or naphthalene ring which is unsubstituted or substituted with alkoxy, alkyl, aralkyl, or a halogen. The number of carbon atoms in the substituent is preferably not more than about 18, more preferably not more than 9, and most preferably not more than 3. Accordingly, $Ar_1OH$ as phenols preferably represents a phenol or naphthol derivative with a substituent having carbon atoms as described above, and more preferably represents a phenol or naphthol. $R_3$ and $R_4$ preferably each represents a straight or branched alkylene or oxaalkylene group having from 1 to 10 carbon atoms and preferably from 2 to 6 carbon atoms, or a group thereof which may have a substituent (e.g., alkyl, aryl, alkoxy, halogen, and acyloxy). That is, $HO-R_4-OH$ and $Ar_2OR_3OH$ as alcohols, which are preferably used in the present invention, represent alkylenediol, alkenylenediol, and alkyndiol, and aryloxyalkanol, respectively.

Examples of the aryloxy group ($Ar_1O—$ and $Ar_2O—$) are phenoxy, tolyloxy, xylyloxy, trimethylphenoxy, p-ethylphenoxy, tetramethylphenoxy, chlorophenoxy, chloromethylphenoxy, fluoromethylphenoxy, trifluoromethyldimethylphenoxy, thiomethoxyphenoxy, chlorobromophenoxy, naphthoxy, cumylphenoxy, p-fluorophenoxy, allylphenoxy, o-methoxyphenoxy, p-methoxyphenoxy, ethoxyphenoxy, p-butoxyphenoxy, methoxytolyloxy, trimethylnaphthoxy, tert-butylphenoxy, p-cyanophenoxy, tert-amylphenoxy, n-dodecylphenoxy, dodecylnaphthoxy, chloronaphthoxy, benzylphenoxy, benzyloxyphenoxy, fluorophenoxy, tetrafluorophenoxy, benzyloxyethoxy, β-phenoxyethoxyphenoxy, 4-methylthiophenoxy, and 4-ethylthiophenoxy.

In connection with $Ar_2OR_3OH$, the number of carbon atoms in the alkanol portion is preferably not more than 12, more preferably not more than 8, and most preferably not more than 4. This may be straight or branched.

As described above, it may have any other substituent as long as it contains at least one aryloxy group.

Examples include β-aryloxy-substituted alkanol, α-aryloxy-substituted alkanol, γ-aryloxy-substituted alkanol, Γ-aryloxy-substituted alkanol, β-aryloxy-substituted alkanol, ω-aryloxy-substituted alkanol, ω-aryloxy-substituted alkoxylalkanol, aryloxy-substituted halo-alkanol, aryloxy-substituted alkoxyalkanol, and aryloxy-substituted hydroxyalkanol. Of these compounds, β- and ω-substituted compounds are particularly preferred.

$R_3$ and $R_4$ preferably each represents $—C_nH_m—$ or $—C_nH_m—O—C_nH_m—$ (wherein m is 2n or 2n−2), and n and m are preferably from 1 to 10 and from 2 to 22, respectively. Particularly preferred are $—CH_2CH_2—$, $—C_4H_8—$, $—C_3H_6—$, $—CH_2CH(CH_3)—$, $—CH_2—CH=CH—CH_2—$, $—CH_2CH(C_2H_5)—$, $—CH_2CH(C_6H_5)—$, $—CH_2OCH_2OCH_2—$, $—C_2H_4OCH_2OC_2H_4—$, $—C_2H_4OC_2H_4—$, $—CH_2CH(CH_2Cl)—$, $—CH_2—C\equiv C—CH_2—$, etc.

$R_2SO_2X$ in the present invention represents an aliphatic or aromatic sulfonyl chloride, and preferably aromatic sulfonyl chloride. This compound can be prepared by reacting an aliphatic or aromatic compound with chlorosulfonic acid, or by acting a chlorinating agent onto a sulfonic acid. Specifically, the number of carbon atoms of the sulfonyl chloride is not more than 16, and preferably from 1 to 8. Examples of the sulfonyl chloride are triisopropylnaphthalenesulfonyl chloride, ethylnaphthalenesulfonyl chloride, dimethylnaphthalenesulfonyl chloride, isopropylnaphthalenesulfonyl chloride, naphthalenesulfonyl chloride, toluenesulfonyl chloride, benzenesulfonyl chloride, 1,3-benzenedisulfonyl chloride, chlorobenzenesulfonyl chloride, ethylhexanesulfonyl chloride, methanesulfonyl chloride, butanesulfonyl chloride, hexanesulfonyl chloride, and p-toluenesulfonyl chloride. Particularly preferred is p-toluenesulfonyl chloride. This compound has many advantages, for example, it is excellent in reactivity and stability in an inorganic base-polar solvent, it has not inhibited the etherification reaction, and it is easy to handle.

Representative examples of the base(alkali) include caustic soda, caustic potash, sodium carbonate, and potassium carbonate. Particularly preferred are caustic soda (sodium hydroxide) and caustic potash (potassium hydroxide).

As the polar solvent having a boiling point of not less than 65° C. that is used in the present invention, solvents having a hydrophilic group such as ether, carbonyl, sulfonyl, cyano, and amido are particularly preferred. But solvents having hydroxy group are not suitable.

Preferred examples of the polar solvents include methyl ethyl ketone, tetrahydrofuran, acetonitrile, dimethylacetamide, acrylonitrile, N-methylpyrrolidone, vinylpyrrolidone, dimethoxypropane, hexamethylphosphoramide, sulforane, cyclohexanone, methyl isobutyl ketone, and methylcyclohexanone. In particular, water-soluble solvents are preferred in view of ease in post-treatment.

Strangely, however, when dimethylformamide and dimethylsulfoxide, which are preferably used in a process for the preparation of ethers by reacting halides in the presence of alkali are used in the present invention, good results cannot be obtained.

These solvents are used in such a manner that the solid content is not less than 10%, and preferably not less than 20 wt%.

It is preferred for the solvents to be used in combination with a small amount of water from viewpoints of dissolution of the inorganic base, and sulfonic acid salt, and of prevention of by-production of colored matter. Furthermore, from a viewpoint of preventing coloration of the liquid, it is preferred to carry out the reaction in an inert gas.

In the practice of the reaction, a crown ether and a phase transfer catalyst may be used.

Since the reaction of the present invention is a reaction of the active halide in the inorganic base-polar solvent, a competitive reaction between the esterification reaction and the hydrolysis reaction of the acid halide occurs, thereby reducing the yield and making difficult the purification. In view of this fact, it is preferred to control the reaction temperature of the system to not more than 150° C. Specifically, the esterification reaction is carried out at a temperature of from −20° C. to 70° C. and preferably from 0° C. to 50° C., and the etherification reaction is carried out at a temperature of from 30° C. to 150° C. and preferably from 60° C. to 110° C.

The amount of $R_2SO_2X$ used in preparing the ethers of the present invention according to the scheme (I) is from 0.8 to 2 mols, particularly preferably from 1 to 1.5 mols per mol of $R_1OH$. The amount of $Ar_1OH$ used is preferably from 0.8 to 2 mols, particularly preferably from 1 to 1.2 mols per mol of $R_1OH$. The amount of the base used is preferably from 1.8 to 6 mols, and particularly preferably from 2 to 4 mols per mol of $R_1OH$.

In preparing ethers of the present invention according to the scheme (II), an intermediate product, alkylenediol disulfonate, may be separated, or it may be directly reacted with phenols without its isolation. In the former case that the intermediate product is separated, the amount of $R_2SO_2X$ used in the esterification reaction is preferably from 2 to 4 mols, and particularly preferably from 2 to 3 mols per mol of $HO-R_4-OH$. The amount of the bases used is preferably from 2 to 8 mols, and particularly preferably from 2 to 4 mols per mol of $HO-R_4-OH$. On the other hand, the amount of $Ar_1OH$ used in the etherification reaction is preferably from 2 to 4 mols, and particularly preferably from 2 to 3 mols per mol of $R_2SO_2O-R_4-OSO_2-R_2$. The amount of the bases used is preferably from 2 to 6 mols, particularly preferably from 2 to 4 mols per mol of $R_2SO_2O-R_4-OSO_2-R_2$. In a case that the reaction is carried out without isolating the alkylenediol disulfonate, the amount of $R_2SO_2X$ used is preferably from 2 to 4 mols, particularly preferably from 2 to 3 mols per mol of $HO-R_4-OH$. The amount of $Ar_1OH$ used is preferably from 2 to 4 mols, particularly preferably from 2 to 3 mols per mol of $HO-R_4-OH$. The amount of the base used is preferably from 4 to 12 mols, and particularly preferably from 4 to 8 mols per mol of $HO-R_4-OH$. This process is preferred.

The process of preparation of ethers of the present invention is illustrated in Examples 1 to 36, and a heat-sensitive recording material using ethers as obtained by the present invention is shown in Example 37.

EXAMPLE 1

50 ml of acetonitrile, 0.1 mol of phenoxy ethanol, and p-toluenesulfonyl chloride were placed in a flask equipped with a stirrer. A 48 wt% aqueous solution of caustic soda (0.22 mol equivalent) was added dropwise at room temperature while stirring and the resulting mixture was held for 20 minutes taking care so that the inner temperature did not exceed 65° C.

Subsequently, 0.1 mol of p-ethylphenol was slowly added and the resulting mixture was stirred at from 85° C. to 95° C. for 2 hours. The reaction mixture was allowed to cool. On pouring the reaction mixture at about 40° C. in a mixed solvent of methanol and water, crystals precipitated. 1-Phenoxy-2-p-ethylphenoxyethane having a purity as determined by liquid chromatography of more than 99.9% and a melting point of 107°–108° C. was obtained. The yield was 96%.

EXAMPLES 2 to 5

The same procedure as in Example 1 was repeated, except that the acetonitrile was replaced by methyl ethyl ketone (Example 2), N-methylpyrrolidone (Example 3), hexamethylphosphoramide (Example 4), or sulforane (Example 5), respectively. The desired product was obtained in a yield of from 92% to 97%. In particular, the use of N-methylpyrrolidone, hexamethylphosphoramide, and sulforane are preferred in that the reaction is nearly completed on stirring for about 15 minutes after the dropwise addition of p-ethylphenol.

EXAMPLES 6 to 20

Ether derivatives were prepared in the same manner as in Example 1 using the starting materials shown in Table 1. The starting materials used, and the products and their melting points are shown in Table 1. The yield was from 85% to 95%.

TABLE 1

| Example No. | R₁OH | Ar₁OH | Products | Melting Point (°C.) |
|---|---|---|---|---|
| 6 | C₆H₅—OCH₂CH₂OH | HO—C₆H₄—OCH₃ | C₆H₅—OCH₂CH₂O—C₆H₄—OCH₃ | 102–104 |
| 7 | 2-CH₃-C₆H₄—OC₂H₄OH | HO—C₆H₄—OC₂H₅ | 2-CH₃-C₆H₄—OCH₂CH₂O—C₆H₄—OC₂H₅ | 100–101 |
| 8 | C₆H₅—OCH₂CH₂OH | HO—C₆H₃(t-C₄H₉)—OH | C₆H₅—OCH₂CH₂O—C₆H₃(t-C₄H₉)—OH | 98–99.5 |
| 9 | 3-CH₃-C₆H₄—OCH₂CH₂OH | HO—C₆H₄—CH₃ | 3-CH₃-C₆H₄—OCH₂CH₂O—C₆H₄—CH₃ | 98 |
| 10 | C₆H₅—OCH₂CH₂OH | HO—C₆H₄—CH₃ | C₆H₅—OCH₂CH₂O—C₆H₄—CH₃ | 100–101.5 |
| 11 | " | HO—C₆H₄—F | C₆H₅—OCH₂CH₂O—C₆H₄—F | 90–93 |
| 12 | " | HO—C₆H₅ | C₆H₅—OCH₂CH₂O—C₆H₅ | 94–96 |
| 13 | " | HO—C₆H₄—C₆H₁₁ | C₆H₅—OCH₂CH₂O—C₆H₄—C₆H₁₁ | 128–129 |
| 14 | " | HO—C₆H₄—CH(CH₃)₂ | C₆H₅—OCH₂CH₂O—C₆H₄—CH(CH₃)₂ | 95–95.5 |
| 15 | " | HO—C₆H₄—OH | C₆H₅—OCH₂CH₂O—C₆H₄—OCH₂CH₂O—C₆H₅ | 184–185 |
| 16 | H₃C—C₆H₄—OCH₂CH₂OH | HO—C₆H₄—F | H₃C—C₆H₄—OCH₂CH₂O—C₆H₄—F | 106–107 |
| 17 | 3-CH₃-C₆H₄—OCH₂CH₂OH | HO—C₆H₄—OCH₃ | 3-CH₃-C₆H₄—OCH₂CH₂O—C₆H₄—OCH₃ | 113–114 |
| 18 | C₂H₅—C₆H₄—OCH₂CH₂OH | HO—C₆H₄—Cl | C₂H₅—C₆H₄—OCH₂CH₂O—C₆H₄—Cl | 97–98 |
| 19 | 2-OCH₃-C₆H₄—OCH₂CH₂OH | CH₃O—C₆H₄—OH | 2-OCH₃-C₆H₄—OCH₂CH₂O—C₆H₄—OCH₃ | 138–139 |
| 20 | 2-naphthyl—OCH₂CH(CH₃)OH | HO—C₆H₄—OCH₃ | 2-naphthyl—OCH₂CH(CH₃)O—C₆H₄—OCH₃ | 104–105 |

65

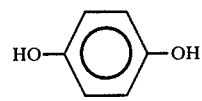
HO—C₆H₄—OH

In Example 15 only, was used in an amount of 0.5 mol.

EXAMPLE 21

100 ml of acetonitrile, 0.1 mol of 1,4-butanediol, and 0.22 mol of p-toluenesulfonic acid chloride were placed in a flask equipped with a stirrer.

A 48 wt% aqueous solution of caustic soda (0.6 mol equivalent) was added dropwise as quickly as possible at an inner temperature of not more than 35° C. while stirring. Then the mixture was held for 30 minutes taking care so that the inner temperature did not exceed 60° C. Subsequently, a solution of 0.22 mol of phenol in acetonitrile was slowly added dropwise, and the resulting mixture was stirred for 3 hours while refluxing. On pouring the reaction mixture into a methanol-water mixture, crystals precipitated. These crystals were separated by filtration and then washed with methanol to yield 1,4-diphenoxybutane. The yield was 81%.

In this single bath method, dimethylformamide and dimethylsulfoxide which are not polar solvents as defined in the present invention, but are generally said to be polar solvents, did not yield good results.

EXAMPLES 22 to 28

Ether derivatives were prepared in the same manner as in Example 21, except that the starting materials shown in Table 2 were used. The starting materials, and the products and their melting points are shown in Table 2. The yields were from 73% to 88%.

were placed in a flask equipped with a stirrer. A 48 wt% aqueous solution of caustic soda (0.12 mol equivalent) was added dropwise at an inner temperature of not more than 75° C. while stirring. The mixture was stirred while refluxing for 2 hours. The reaction mixture was allowed to cool. On pouring the reaction mixture at about 40° C. into a methanol-water mixture, crystals precipitated. These crystals were separated by filtration, and then dried to yield 1-phenoxy-2-p-ethylphenoxyethane (m.p., 107°-108° C.). The yield was 98%.

EXAMPLE 30

100 ml of acetonitrile, 0.12 mol of 1,3-propanediol and 0.27 mol of p-toluenesulfonyl chloride were placed in a flask equipped with a stirrer. A 48 wt% aqueous solution of caustic soda (0.4 mol equivalent) was added dropwise as quickly as possible at an inner temperature of not more than 35° C. while stirring. Then the mixture was held for 30 minutes taking care so that the inner temperature did not exceed 60° C. On pouring the mixture into water, 1,3-bis-p-tolysulfonyloxypropane was obtained in the form of white crystals. These crystals were separated by filtration and dried.

Subsequently, 100 ml of acetonitrile, 0.1 mol of 1,3-di-p-tolysulfonyloxypropane and 0.22 mol of p-cresol were placed in a flask equipped with a stirrer. A 48 wt% aqueous solution of caustic soda (0.3 mol equivalent) was added dropwise taking care so that the inner tem-

TABLE 2

| Example No. | HO—R₃—OH | HO—Ar₁ | Products | Melting Point (°C.) |
| --- | --- | --- | --- | --- |
| 22 | HO—(CH₂)₄OH | HO—⟨○⟩—CH₃ | CH₃—⟨○⟩—O(CH₂)₄O—⟨○⟩—CH₃ | 102 |
| 23 | HO—(CH₂)₈OH | HO—⟨○⟩—OCH₃ | CH₃O—⟨○⟩—O(CH₂)₈O—⟨○⟩—OCH₃ | 132–133 |
| 24 | HO—(CH₂)₃OH | HO—⟨○⟩—CH₃ | CH₃—⟨○⟩—O(CH₂)₃O—⟨○⟩—CH₃ | 93 |
| 25 | ″ | HO—⟨○⟩—OCH₃ | CH₃O—⟨○⟩—O(CH₂)₃O—⟨○⟩—OCH₃ | 89–90 |
| 26 | HOC₂H₄OC₂H₄OH | HO—⟨○⟩—OCH₃ | CH₃O—⟨○⟩—OC₂H₄OC₂H₄O—⟨○⟩—OCH₃ | 101 |
| 27 | ″ | HO—⟨○⟩—OC₂H₅ | C₂H₅O—⟨○⟩—OC₂H₄OC₂H₄O—⟨○⟩—OC₂H₅ | 98 |
| 28 | ″ | HO—⟨○⟩—⟨○⟩ | ⟨○⟩—⟨○⟩—OC₂H₄OC₂H₄O—⟨○⟩—⟨○⟩ | 161 |

EXAMPLE 29

50 ml of acetonitrile, 0.1 mol of phenoxyethanol and p-toluenesulfonyl chloride were placed in a flask equipped with a stirrer. A 48 wt% aqueous solution of caustic soda (0.2 mol equivalent) was added dropwise while stirring, and the resulting mixture was held for 25 minutes taking care so that the inner temperature did not exceed 80° C. On pouring the mixture into water, β-phenoxyethyl-p-tosylate (m.p., 80°-81° C.) was obtained in the form of white crystals. The yield was 92%.

Subsequently, 50 ml of acetonitrile, 0.092 mol of β-phenoxyethyl-p-tosylate, and 0.1 mol of p-ethylphenol perature did not exceed 75° C. while stirring. The mixture was stirred while refluxing for 3 hours. On pouring the reaction mixture into a methanol-water mixture, crystals precipitated. These crystals were separated by filtration and washed with methanol to obtain 1,3-di-p-tolyoxypropane (m.p., 93°-94° C.). The yield was 92%.

EXAMPLE 31

1,4-Di-p-tolyoxybutane (m.p., 102°-103° C.) was prepared in the same manner as in Example 30, except that 1,4-propanediolsulfonyloxybutane was used in place of the 1,3-butanediol in Example 30. The yield was 90%.

EXAMPLE 32

1,4-Diphenoxybutane (m.p., 98°–99° C.) was prepared in the same manner as in Example 31, except that phenol was used in place of p-cresol in Example 31. The yield was 93%.

EXAMPLE 33

1,4-Di-p-chlorophenoxybutane (m.p., 104°–105° C.) was prepared in the same manner as in Example 31, except that p-chlorophenol was used in place of the p-cresol in Example 31. The yield was 93%.

EXAMPLES 34 to 36

The same procedure as in Example 32 was repeated, except that the acetonitrile was replaced with methyl ethyl ketone (Example 34), N-methylpyrrolidone (Example 35), or sulforane (Example 36), respectively. The yields were from 90% to 95%. Particularly, when N-methylpyrrolidone and sulforane were used, the reaction rate was high; it has been found that the use of N-methylpyrrolidone and sulforane was especially favorable. Accordingly it has been found that the desired ethers can be obtained in high yield by the process of the present invention.

EXAMPLE 37

A heat-sensitive recording material was prepared using an ether prepared by the process of the present invention.

2.5 g of 2-anilino-3-chloro-6-diethylaminofluorane as electron-donating colorless dye, 2.5 g of 2-anilino-3-methyl-6-N-methyl-N-isoamylaminofluorane, and 35 g of a 5 wt% aqeuous solution of polyvinyl alcohol (saponification value: 99%; degree of polymerization: 1,000) were dispersed in a sand mill. Separately 10 g of bisphenol A as an electron-receiving compound and 100 g of a 5 wt% aqueous solution of polyvinyl alcohol were dispersed in a sand mill.

In addition, 15 g of each of the ethers obtained in Examples 1 and 6 was dispersed along with 2 wt% polyvinyl alcohol in a horizontal sand mill to prepare a dispersion having a particle diameter of 2 μm. Each of the thus-obtained ether dispersion was mixed with two dispersions prepared above, and then 20 g of kaolin (Georgia kaolin) was added and thoroughly dispersed therein. In addition, 4.5 g of a 50 wt% paraffin wax emulsion dispersion (Cellosol #428 produced by Chukyo Yushi Co., Ltd.) was added to prepare coating liquids.

These coating liquids were coated on a neutral paper having a basis weight in such a manner that the amount (calculated as solids) coated was 5.2 g/m$^2$, dried at 60° C. for 1 minute, and then subjected to a super-calendering treatment at a linear pressure of 60 kgW/cm to produce samples 1 and 2, respectively.

Sample No. 3 was also prepared in the same manner as above, except that an ether was not added.

This coated paper was colored by heating it at a heating energy of 250 mJ/mm$^2$ in order to evaluate the color density properties. The results are shown in Table 3.

TABLE 3

| Sample | Ether | Color Density |
| --- | --- | --- |
| 1 | Ether of Example 1 | 1.05 |
| 2 | Ether of Example 6 | 1.12 |
| 3 | none | 0.32 |

Note:
Sample No. 3 - comparative example

It can be seen from the results of Table 3 that the ethers prepared by the process of the present invention are useful in increasing the sensitivity.

While the invention has been described in detail and with reference to specific embodiments thereof, it will be apparent to one skilled in the art that various changes and modifications can be made therein without departing from the spirit and scope thereof.

What is claimed is:

1. A process for preparing a polyether comprising reacting an alcohol which is a diol or an aryloxyalkanol with an organic sulfonyl halide in a solvent in the presence of an alkali to form a reaction mixture containing a sulfonate, and then reacting the sulfonate with a phenol, wherein the alkali is an inorganic base selected from hydroxides and carbonates of sodium and potassium, and the solvent is a polar solvent.

2. A process as in claim 1, wherein the organic sulfonyl halide is an aromatic sulfonyl halide having from 6 to 8 carbon atoms.

3. A process as in claim 1, wherein the organic sulfonyl halide is aromatic sulfonyl chloride.

4. A process as in claim 1, wherein the alkali is sodium hydroxide or potassium hydroxide.

5. A process as in claim 1, wherein the polar solvent has as a hydrophilic group, an ether group, a carbonyl group, a cyano group, a sulfonyl group, or an amido group, and has a boiling point of not less than 65° C.

6. A process as in claim 1, wherein the reaction wherein the alcohol is reacted with the organic sulfonyl halide to prepare a sulfonate is carried out at a temperature of from −20° C. to 70° C., and the reaction wherein the sulfonate is reacted with a phenol to form an ether is carried out at a temperature of from 30° C. to 150° C.

7. A process as in claim 1, wherein the alcohol is alkylenediol.

8. A process as in claim 1, wherein the alcohol is aryloxyalkanol.

9. A process as in claim 1, wherein the phenol is a phenol or naphthol derivative with a substituent having 9 or less carbon atoms.

10. A process as in claim 1, wherein the phenol is a phenol or naphthol derivative with a substituent having 3 or less carbon atoms.

11. A process as in claim 5, wherein the polar solvent is selected from the group consisting of methyl ethyl ketone, tetrahydrofuran, acetonitrile, dimethylacetamide, acrylonitrile, N-methylpyrrolidone, vinylpyrrolidone, dimethoxypropane, hexamethylphosphoramide, sulforane, cyclohexanone, methyl isobutyl ketone, and methylcyclohexanone.

12. A process for preparing a polyether comprising reacting an alcohol which is a diol or an aryloxyalkanol with an organic sulfonyl halide in a solvent in the presence of an alkali to form a reaction mixture containing a sulfonate, and then without isolating the sulfonate, reacting the sulfonate with a phenol, wherein the alkali is an inorganic base selected from hydroxides and carbonates of sodium and potassium, and the solvent is a polar solvent.

13. A process as in claim 1, wherein the phenol is a phenol or naphthol.

14. A process as in claim 1, wherein the diol is an alkyndiol.

15. A process as in claim 1, wherein the diol is an alkenlyenediol.

16. A process as in claim 1, wherein the diol is an aryloxyalkanol, the amount of the organic sulfonyl halide used in preparing the polyether is from 0.8 to 2 mols per mol of aryloxyalkanol, the amount of base used is from 1.8 to 6 mols per mol of aryloxyalkanol, and the phenol is a phenol or naphthol and is used in an amount of from 0.8 to 2 mols per mol of aryloxyalkanol.

17. A process as in claim 16, wherein the amount of the organic sulfonyl halide is from 1.0 to 1.5 mols per mol of aryloxyalkanol, the amount of base used is from 2 to 4 mols per mol of aryloxyalkanol, and the phenol is used in an amount of from 1 to 1.2 mols per mol of aryloxyalkanol.

18. A process as in claim 1, further comprising isolating the sulfonate from the reaction mixture before reacting the sulfonate with the phenol, and wherein the alcohol is a diol, and the reaction of the diol with the halide produces a disulfonate, the amount of the organic sulfonyl halide used is from 2 to 4 mols per mol of diol, the amount of base used during the reaction of the diol with the halide is from 2 to 8 mols per mol of diol, the phenol is a phenol or napthanol and is used in an amount of 2 to 4 mols per mol of disulfonate and the amount of base used during the reaction of the phenol with the disulfonate is from 2 to 6 mols per mol of the disulfonate.

19. A process as in claim 18, wherein the amount of the halide is from 2 to 3 mols per mol of diol, the amount of base used during the reaction of the diol with the halide is from 2 to 4 mols per mol of diol, the phenol is used in an amount of 2 to 3 mols per mol of disulfonate, and the amount of base used in the reaction of the phenol with the disulfonate is from 2 to 4 mols per mol of disulfonate.

20. A process as in claim 12, wherein the alcohol is a diol, the amount of the organic sulfonyl halide used is from 2 to 4 mols per mol of diol, the amount of base used is from 4 to 12 mols per mol of diol, the phenol is a phenol or naphthol and is used in an amount of from 2 to 4 mols per mol of diol.

21. A process as in claim 20, wherein the amount of the organic sulfonyl halide used is from 2 to 3 mols per mol of diol, the amount of base used is from 4 to 8 mols per mol of diol, and the phenol is used in an amount of from 2 to 3 mols per mol of diol.

22. A process as in claim 12, wherein the reaction in which the alcohol is reacted with the organic sulfonyl halide to prepare a sulfonate is carried out at a temperature of from $-20°$ C. to $70°$ C., and the reaction wherein the sulfonate is reacted with the phenol is carried out at a temperature of from $30°$ C. to $150°$ C.

23. A process as claimed in claim 22, wherein the alcohol is a diol, the amount of the organic sulfonyl halide used is from 2 to 4 mols per mol of diol, the amount of base used is from 4 to 12 mols per mol of diol, the phenol is a phenol or naphthol and is used in an amount of from 2 to 4 mols per mol of diol.

24. A process as in claim 18, wherein the reaction in which the alcohol is reacted with the organic sulfonyl halide to prepare a sulfonate is carried out at a temperature of from $-20°$ C. to $70°$ C., and the reaction wherein the sulfonate is reacted with a phenol is carried out at a temperature of from $30°$ C. to $150°$ C.

* * * * *